United States Patent [19]

Kitahara

[11] Plant 4,329

[45] Oct. 31, 1978

[54] GRAPEVINE

[76] Inventor: Toru Kitahara, 86600 Avenue 72, Thermal, Calif. 92274

[21] Appl. No.: 863,852

[22] Filed: Dec. 23, 1977

[51] Int. Cl.[2] ..... A01H 5/03

[52] U.S. Cl. ..... Plt./47

[58] Field of Search ..... Plt./47

*Primary Examiner*—Robert E. Bagwill

*Attorney, Agent, or Firm*—Huebner & Worrel

[57] ABSTRACT

A grapevine generally similar to the Perlette unpatented grapevine but which bears grapes which ripen approximately 10 days later than the Perlette and 15 days earlier than the Thompson Seedless unpatented grapevine, and which are somewhat pear shaped and exceptionally crisp.

3 Drawing Figures

BACKGROUND OF THE VARIETY

The present invention relates to a new and distinct variety of grapevine which is generally similar to the Perlette but which is distinguished therefrom by bearing grapes which ripen approximately 10 days later, which are somewhat pear shaped and exceptionally crisp.

Like the grapes of the grapevines of U.S. Plant Pat. Nos. 1,250 to Fujihara and 2,335 to Folmar the grapes of the new variety are of the so-called white table grape class of grapes and are seedless.

ORIGIN AND REPRODUCTION

The new variety of grapevine was discovered in the applicant's vineyard of Perlette grapevines at 86600 Avenue 72, Thermal, Calif., where it was also reproduced by the applicant by grafting and by cuttings and after such asexual reproduction was found to maintain its distinctive characteristics. It appeared in the Perlette vineyard as a complete grapevine and is believed to have resulted from a sport of the Perlette. It attracted the applicant's attention by ripening approximately 10 days later than the Perlettes in the same vineyard. The applicant also observed that its grapes were of excellent quality, good taste, somewhat pear shaped, and exceptionally hard and crisp.

DRAWING

The new variety is illustrated in the accompanying drawing which consists of a montage of color photographs in which:

The upper photograph is a side view of a vine of the present variety immediately before harvest which has been treated with gibberellin and had its bunches of grapes trimmed to shape all in accordance with known cultural practices for table grapes.

The lower left photograph shows several grapes characteristic of the present variety.

The lower right photograph is a somewhat enlarged view of a single grape of the present variety.

DETAILED DESCRIPTION

The following is a detailed description of the pomological characteristics of the subject variety with color terminology in accordance with the Nickerson Color Fan, where given by combined numeral-letter designation. Where dimensions, sizes, colors and other characteristics are given, it is to be understood that such characteristics are approximations of averages as they appear under the ecological conditions prevailing in the applicant's designated vineyard near Thermal, Calif.

Vine:

*Size.*—Medium to large.

*Growth.*—Medium.

*Productivity.*—Medium, regular.

*Canes.*—Medium. Joints: More closely spaced than usual. Average spacing. 7.5 to 12.7 cm. Tendrils: Slender, medium-long. Multiple forked. Color: Mature like Perlette, tan to light brown.

Foliage:

*Leaves.*—Many. Petiolar sinus wide V-shape. Three lobe shallow sinus — medium size 17.8 cm.

Flowers:

*Number.*—Abundant.

*Length of blooming season.*—April 5 to April 10.

*Blossom color.*—Same as Perlette. Light yellow. Chartreuse anthers. No petals.

*Shape and size of cluster.*—Untrimmed bunches, wide, long and tapering. Usually shaped by trimming.

*Average length of cluster stem (Peduncle).*—3.8 cm.-5 cm.

*Reproduction organs.*—Stamens: Medium. Filaments: Medium. Pollen: Abundant, very high like Perlette.

Grapes:

*Maturity.*—Approximate dates: 9 or 11 days later than Perlette, June 13-16, 12 to 17 days earlier than Thompson Seedless. With what other varieties: Between Perlette and Thompson Seedless.

*Size of berry.*—Medium.

*Diameter.*—Natural 0.65 cm.-1.6 cm. Treated with Gibberellin and Girdled 1.3 cm.-2.0 cm.

*Length.*—Natural 0.65 cm.-2.5 cm. Treated with Gibberellin and Girdled 1.9 cm.-3.25 cm.

*Shape.*—Longer than Perlette. Frequently pear shaped.

*Average number of clusters to vine.*—40 natural usually thinned to 20 or 25.

*Average number of berries to cluster.*—300-400 natural. 125-150 after thinning.

*Number of seeds to berry.*—None.

*Productivity.*—Heavy.

*Skin.*—Tight.

*Color.*—Brilliant yellow green 2.5 GY, to Brilliant greenish yellow 7.5 Y 9/8.

*Ripening.*—Begins: Approximately May 17. Peak: June 1. End: Fully ripened approximately June 15.

*Clusters ripen.*—Unevenly.

*Texture.*—Hard and very crisp.

*Flavor.*—Excellent — neutral to slightly vinous.

*Aroma.*—None.

*Eating quality.*—Palatability excellent.

*Juice quality.*—Minor.

*Shipping quality.*—Good. Grapes remain hard and crisp. Minor shattering. Less than Thompson Seedless.

*Storing quality.*—Holds well for 30 days at 40° F. with fruit and stems well preserved.

*Uses.*—Fresh table. Not tested for raisins or wine.

Most unusual characteristics: Its production of unusual pear shaped seedless grapes that remain very firm and crisp for several days following harvest.

Normal variations can be expected under environmental conditions different from those prevailing at Thermal, Calif.

Having described the grapevine of my new variety, I claim:

1. A new and distinct variety of grapevine characterized by its similarity to the Perlette grapevine, which it most nearly resembles, but distinguished therefrom by bearing grapes which ripen approximately 10 days later, are elongated and somewhat pear shaped, and are harder and crisper than the grapes of either the Perlette or the Thompson Seedless.

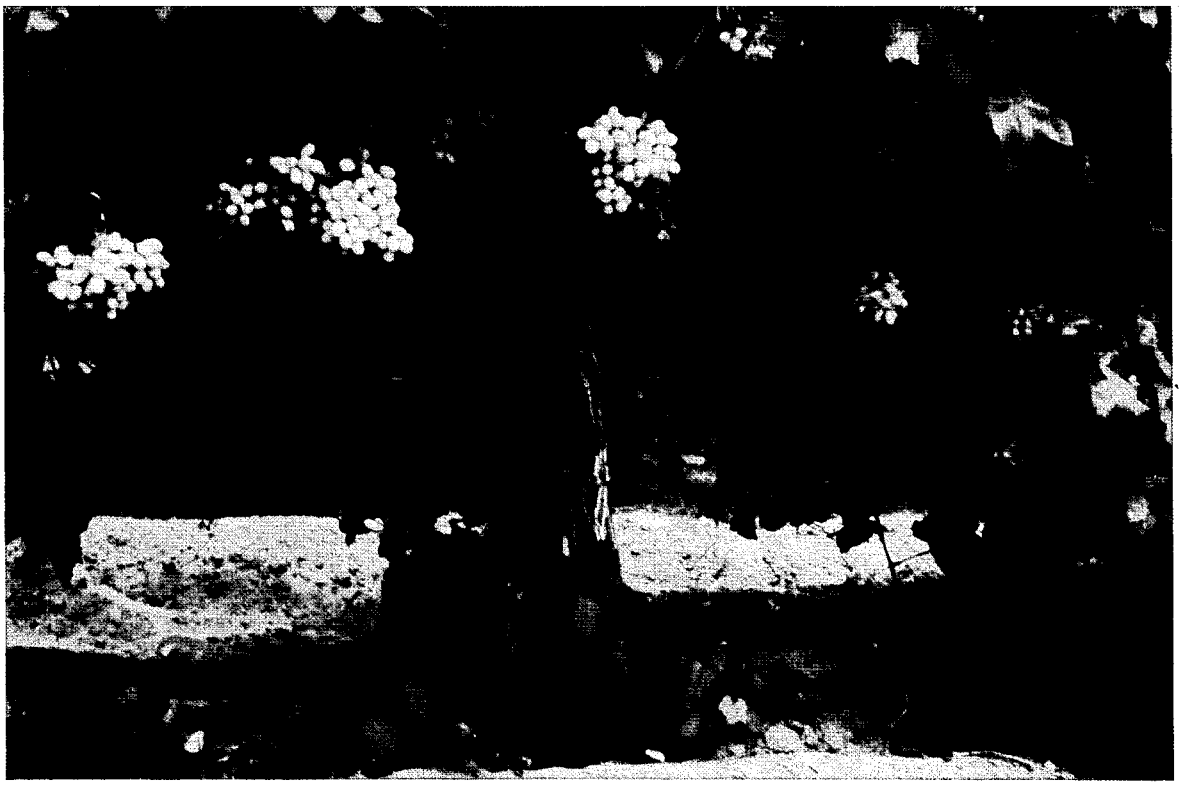
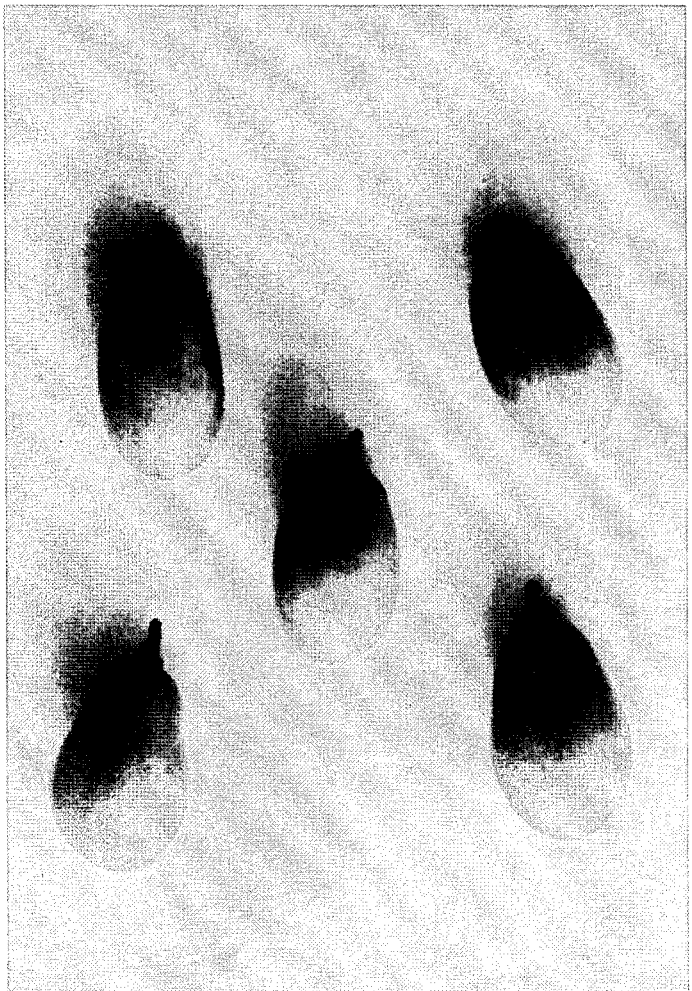
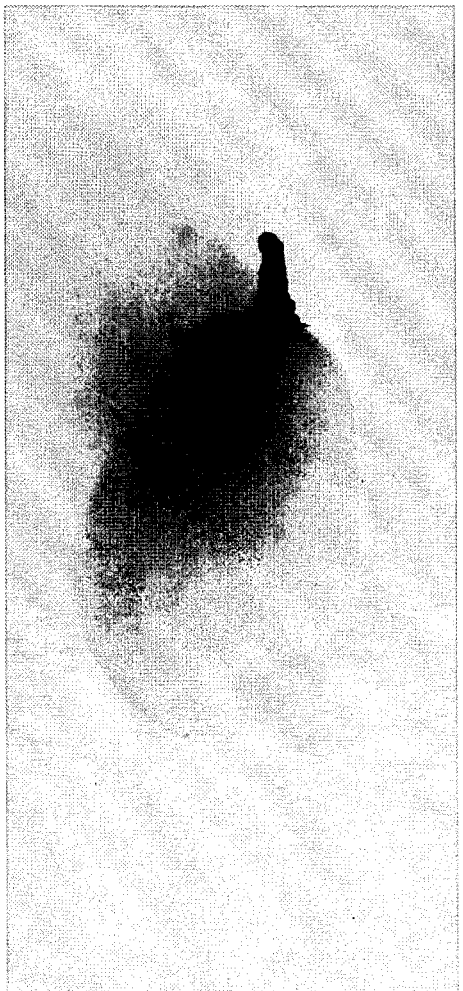

* * * * *